United States Patent [19]
Hering et al.

[11] Patent Number: 5,983,732
[45] Date of Patent: Nov. 16, 1999

[54] INTEGRATED COLLECTION AND VAPORIZATION PARTICLE CHEMISTRY MONITORING

[75] Inventors: Susanne V. Hering, Berkeley; Mark R. Stolzenburg, Albany, both of Calif.

[73] Assignee: Aerosol Dynamics Inc., Berkeley, Calif.

[21] Appl. No.: 09/044,854

[22] Filed: Mar. 20, 1998

Related U.S. Application Data

[60] Provisional application No. 60/041,350, Mar. 21, 1997.

[51] Int. Cl.$^6$ .................................................. G01N 15/00
[52] U.S. Cl. ....................................................... 73/863.22
[58] Field of Search ............................... 73/28.01, 28.04, 73/28.05, 31.07, 863.11, 863.21, 863.22, 864.81; 422/88, 68.1; 250/255, 288; 436/110

[56] References Cited

U.S. PATENT DOCUMENTS

| | | | |
|---|---|---|---|
| 4,117,713 | 10/1978 | Phillips et al. | 73/28.01 |
| 5,110,747 | 5/1992 | Pataschnick et al. . | |
| 5,162,652 | 11/1992 | Cohen et al. . | |
| 5,196,170 | 3/1993 | Pataschnick et al. . | |
| 5,279,970 | 1/1994 | Pataschnick et al. . | |

OTHER PUBLICATIONS

Hering, Susanne V., et al., "Design and Evaluation of New Low–Pressure Impactor", Envir. Sci. & Tech., vol. 12, No. 6, Jun. 1978, pp. 667–673.

Hering, Susanne V., et al., "Origins of Aerosol Sulfur Size Distributions in the Los Angeles Basin", Atmospheric Environment, vol. 16, No. 11, 1982, pp. 2647–2656.

Roberts, P.T., et al., "Analysis of Sulfur in Deposited Aerosol Particles by Vaporization and Flame Photometric Detection", Atmos. Environment, vol. 10, 1976, pp. 403–408.

Simon, Poruthoor K., et al., "Continuous Automated Measurement of Gaseous Nitrous and Nitric Acids and Particulate Nitrite and Nitrate", Envir. Sci. & Tech., vol. 29, No. 6, 1995, pp. 1534–1541.

Stein, Stephen W., et al., "Measurements of Relative Humidity–Dependent Bounce and Density for Atmospheric Particles Using the DMA–Impactor Technique", Atmos. Envir., vol. 28, No. 10, 1994, pp. 1739–1746.

Turpin, B.J., et al., "An In Situ, Time–Resolved Analyzer for Aerosol Organic and Elemental Carbon", Aerosol Sci. and Tech., vol. 12, pp. 161–171, 1990.

Yamamoto, Masatoshi, et al., "Determination of Nitrate in Deposited Aerosol Particles by Thermal Decomposition and Chemiluminsecence", Analytical Chemistry, vol. 66, No. 3, Feb. 1, 1994, pp. 362–367.

*Primary Examiner*—Robert Raevis
*Attorney, Agent, or Firm*—James Creighton Wray; Meera P. Narasimhan

[57] ABSTRACT

An integrated collection and vaporization cell apparatus has a collector and vaporizer cell for collecting airborne particles from sample gas on a collector strip in the cell and a power source connected to the strip for rapidly heating the strip and converting the particles to vapors for analysis without need of removing the strip from the cell. A sample gas director connected to the cell directs sample gas and particles to the collector strip. Particles are collected on the strip by impaction. Rapid heating of the strip vaporizes the particles. A carrier gas flowed into the cell through the director and directly into the cell through a port directs the vapors from the cell to an analyzer port. A measurer connected to the analyzer port measures the amount of vapors and elemental constituents obtained from vaporization of the particles. A humidifier is provided to increase particle collection efficiency. A pre-impactor and denuder are provided to remove large particles and compounds from the sample gas before analysis. A vented housing around the pre-impactor, denuder, humidifier and cell maintains sample gas temperature near ambient temperature. The sample conduit is free of valves.

50 Claims, 5 Drawing Sheets

INTEGRATED COLLECTION AND VAPORIZATION PARTICLE CHEMISTRY MONITORING

This application claims the benefit of U.S. Provisional Application No. 60/041,350, filed Mar. 21, 1997.

BACKGROUND OF THE INVENTION

The atmosphere contains many particles, some of which are derived from anthropogenic sources. Those particles are comprised of various chemical and elemental constituents, including sulfates, nitrates, organic compounds and soot. Data on the chemical composition of airborne particles is needed to understand their origins and sources, and to evaluate the relationships between specific chemical constituents and potential environmental consequences.

With current technology, measurement of the concentration of chemical and elemental constituents of airborne particles involves several steps. First, a sample must be collected by pulling air through a filter or other particle collection device. At the end of the sampling period the particle filter or collection substrate must be removed from the sampler and transported to the laboratory. Finally, the substrate is analyzed for specific chemical species or elements using ion chromatography, X-ray fluorescence or other methods. That approach is the most widely used today. However, it is costly, and often results are not known until months after the sample was collected.

In contrast to particle monitoring, automated instruments are used routinely to measure concentration of specific gaseous pollutants. For ozone, nitrogen oxides and carbon monoxide automated monitors have made it possible to obtain real-time ambient concentration data at reasonable cost. They also provide immediate indications of pollutant levels. A need exists for equivalent, automated monitoring methods for the chemical and elemental constituents of airborne particles.

There are several automated monitors for particle mass available commercially. Those include beta-gauging methods (Macias and Husar, 1976; Dreiheller, Trost and Wendt, 1988; Wedding and Weigand, 1993), quartz crystal microbalance (Olin and Sem, 1971) and tapered element oscillating microbalance (Patashnick and Rupprecht, 1991). Although those instruments are used for monitoring, none provide data on the chemical or elemental composition of the airborne particles.

The older literature contains several references to automated particle monitors for particle sulfate (Coburn and Husar, 1978; Tanner, 1980; Huntzicker, 1986 and Allen, 1988). Those instruments use a flame photometric detector, and are not as stable as is desired for routine monitoring at typical ambient concentrations. To date, their use has been limited to research studies.

More recently, an automated instrument for measuring inorganic species in gases and particles has been reported by Simon and Dasgupta (1995). That instrument collects particles by steam injection and subsequent condensation, and then injects the condensate directly into an on-line ion chromatograph. That instrument is more complicated than the present invention, requiring handling of steam, liquid flows and continued operation of an ion chromatograph. Although the analytical capabilities of that instrument may be useful for research studies it does not seem likely that it will be suitable for routine monitoring applications.

The literature also describes an in-situ analyzer for carbonaceous aerosol (Turpin, Cary and Huntzicker, 1990). That instrument collects particles by filtration, then slowly heats the collected sample and quantitates the evolved carbon dioxide. With that instrument a second, backup filter is used to correct for adsorption of gaseous hydrocarbons onto the filter media. For reasons of cost and complexity, the use of that instrument has been limited.

Aerosol black carbon, operationally defined as optically absorbing particles, is measured by continuously monitoring the darkness of a filter deposit (Hansen, Rosen and Novakov, 1982, 1984). That approach is used in a commercial instrument called the Aethalometer™ (Magee Scientific, Berkeley, Calif.). The Aethalometer™ has been used for air monitoring studies, and provides high time resolution at low concentrations. However, the approach relies on a physical measurement unique to soot-like carbon. That approach cannot be extended to the monitoring of other particle species or elements.

An ambient carbon particulate monitor has been developed by Rupprecht and Patashnick Co. of Albany, N.Y. The monitor is an automated instrument design to measure the concentration of the carbonaceous fraction of airborne particles. It collects particles over a one hour time period, heats the collected sample and quantitates the evolved carbon dioxide using a non-dispersive infrared detector. A limitation is that the instrument collects particles using a conventional impactor which does not efficiently capture particles below 0.15 $\mu$m in diameter. Soot-carbon particles found in the atmosphere are often below that size, and will not be captured. Additionally, that impactor has no provision for collection of solid particles. Because solid particles tend to rebound on the impactor, it is likely that those particles are not efficiently collected by that method. For those two reasons, that instrument may miss a significant portion of the particle carbon mass.

There is therefore a need for automated monitoring instruments for near real-time determination of the concentration of all the major chemical and elemental constituents of airborne particles.

SUMMARY OF THE INVENTION

The present invention provides automated measurement of the concentrations of sulfates, nitrates, carbon and other elemental constituents of airborne particles.

The present invention provides automated, high-time resolution measurement of specified constituents of airborne particles. The particle constituents that may be measured by this method include, but are not limited to, sulfate, nitrate, carbon and other elemental components. The concentration of the specified particle constituent is measured with respect to the volume of air in which the particles are suspended.

The present invention uses an integrated collection and vaporization cell. with this cell airborne particles are collected in a small area onto a metal strip. At the end of the collection period, the particle deposit is vaporized by rapid resistive heating of the metal strip. The evolved gases are transported by a carrier gas to a commercial gas phase analyzer. The resulting peak in the measured gas-phase concentration is integrated to give the mass of the collected constituent.

The carrier gas, vaporization conditions and detector are chosen depending upon the constituent to be analyzed. For example, particle nitrate is determined using a nitrogen carrier gas, low-temperature vaporization and a standard commercial chemiluminescent nitrogen oxide monitor. Sulfate aerosols are quantitated using high temperature vaporization and a commercial pulsed fluorescent analyzer for sulfur dioxide, or a commercial flame-photometric detector for sulfur gases. Carbon aerosols are detected by quantitation of evolved carbon dioxide by non-dispersive infrared detection. Elemental detection by inductively coupled plasma is also possible with the present invention.

The analysis method used in the present invention is based on the concept used in the sulfur flash-volatilization analysis method of Roberts and Friedlander (1976). With their method, the particle sulfur deposited onto a stainless steel strip is volatilized by capacitor discharge across the strip, and quantitated by a gas-phase flame-photometric sulfur analyzer. The flash-volatilization method is able to quantitate sulfur aerosols at the nanogram level.

For many years that sulfur flash-volatilization method has been used in conjunction with a low-pressure impactor to measure the concentration and size distribution of atmospheric sulfate particles (Hering and Friedlander 1982). However, that measurement process is labor-intensive. It is not suitable for automation for two reasons. First, the collection of the sample was done separately from the analysis. After collection, samples must be transferred by hand to a volatilization cell for analysis. Second, the collection methods required that the stainless steel substrates be greased to prevent rebound of particles. Because the grease evaporates during the analysis step substrates could not be directly reused.

The present invention overcomes those limitations to provide a completely automated system. With the preferred integrated collection and vaporization cell, the particle collection and vaporization is done in the same cell. Second, by the use of humidification or other preconditioning prior to collection, particle rebound is minimized without the use of grease. Apart from a pump and valves to switch the air and carrier gas flows, there are no moving mechanical parts.

The integrated particle collection and analysis cell is a key component of the present invention. The particle collection has been tailored to the rapid vaporization analysis that requires that the particles be deposited in a small area on a substrate that can be rapidly heated. With the integrated collection and vaporization cell of this invention, particles are deposited by means of impaction, as was first described by May (1945), and as is used in the low-pressure impactor of Hering et al. (1978, 1979). The present invention also uses humidification to minimize rebound of particles from the collection surface, as studied by Winkler (1974) and Stein et al (1994). It further uses a high-speed, compressible flow impaction jet to allow small particles in the humidified airstream to grow by water condensation, thus enabling their collection.

The prior art (Patashnick) includes an oxidizer as part of the analysis for particulate carbon. The present invention simply vaporizes the sample. For nitrate analysis and for sulfate and elemental analysis the vaporization is done without oxidation. The oxidation state in the particles is already higher than for the vapor species that is analyzed. In one example, the particle species is $NO_3^-$. The gas analyzed is NO and $NO_2$. Alternatively particle sulfate, $SO_4^{-2}$, must be vaporized to $SO_2$ prior to analysis. The gas analyzed has fewer oxygen atoms per molecule than the particles species.

Patashnick for technical reasons uses a closed, recirculating measurement loop for the analysis. Turpin et al, in 1990, described an automated particle carbon analyzer that uses an open path and collects particles by filtration, and then analyzes for carbon by heating the filter and detecting the evolved carbon dioxide. The present invention uses an open analysis path.

None of the prior art has provision for preconditioning the particles to prevent particle rebound on the impactor collection surface.

None of the prior art is configured so as to eliminate the need for a valve on the sample inlet. That is important because particles readily deposit in most valves.

None of the prior art impactors allows for introduction of purge gas into the cell other than through the orifice tube.

The new monitor is for assaying specific chemical or elemental constituents in the particles, such as sulfate or nitrates. The present invention measures specific chemical or elemental constituents. Among unique attributes of the new method and apparatus are:

The new cell vaporizes the collected sample in place, within the collection cell, without oxidation.

The new preconditioning of the sample by addition of a condensible vapor (water), allows prevention of particle rebound without a need to grease the collection surface. That has not previously been incorporated into an automated particle chemistry monitor.

The new flow system allows analyzing of the evolved gases without need to valve off the sample line. That is not true of any other analyzer that uses a collection step followed by an analysis step.

A preferred embodiment of the present invention has been reduced to practice for particle nitrate monitoring. It has been operated unattended in urban areas yielding five and six particle nitrate determinations per hour. Each determination corresponds to ten-minute and eight-minute collections, respectively, followed by analysis steps of less than two minutes. Soon the analysis step will be less than one minute.

These and further and other objects and features of the invention are apparent in the disclosure, which includes the above and ongoing written specification, with the claims and the drawings.

DETAILED DESCRIPTION OF THE DRAWINGS

Figure 1:
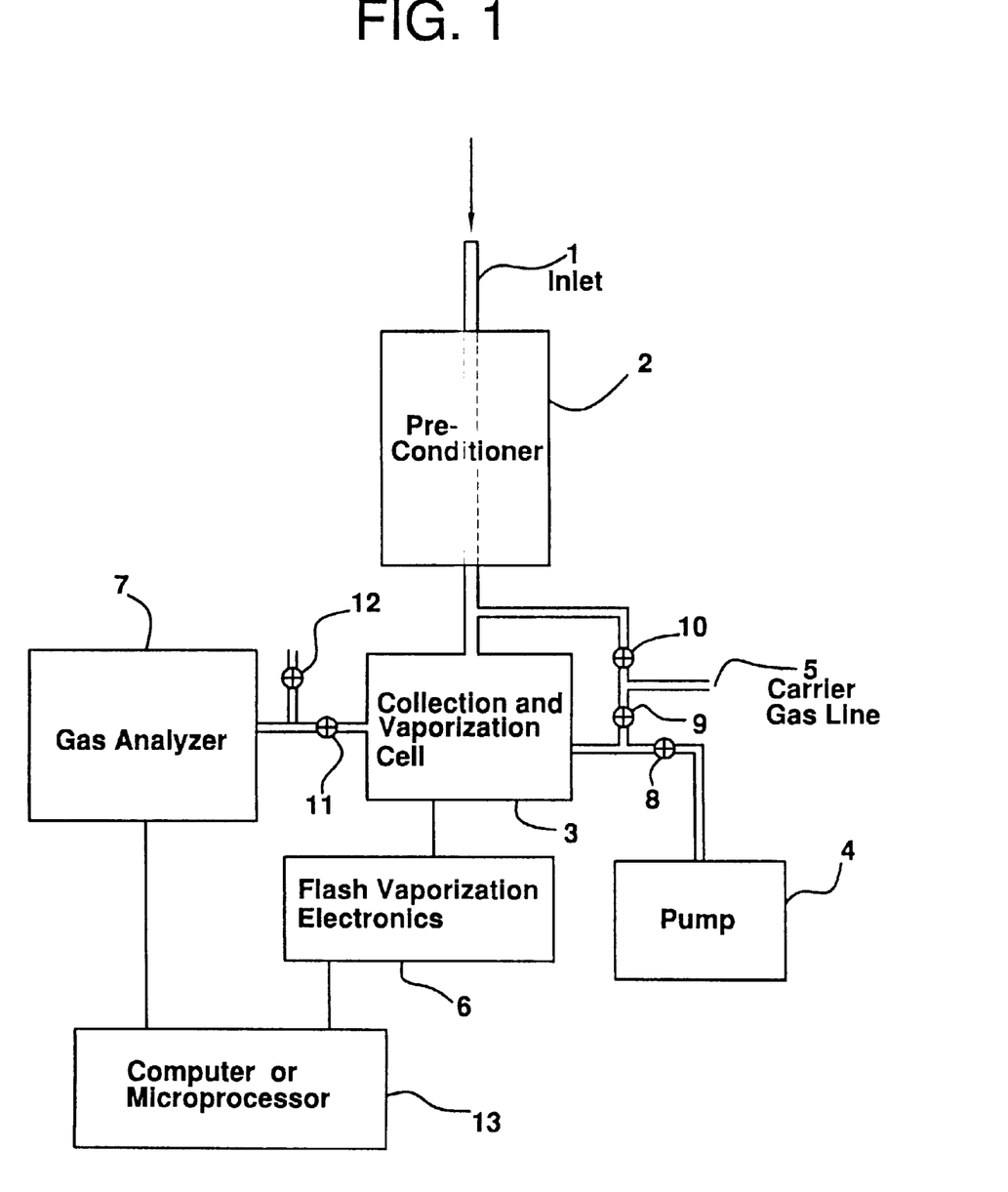
FIG. 1 is a flow diagram showing the major components of the automated sampling and analysis of particles using an integrated collection and vaporization cell.

FIG. 1 shows the preferred components of the system for the automated sampling and analysis of particles. The preferred device has two modes of operation: sampling and analysis.

In the sampling mode the sampled airstream enters at the inlet 1. The airstream passes through a pre-conditioner stage 2, which may contain a precutter to remove coarse particles, or a denuder to remove interfering gaseous species, or a humidifier to enhance particle collection, or any combination of those. The particles in the airstream are then deposited by impaction onto a metal strip housed in the collection and vaporization cell 3. Airflow is provided by the pump 4.

In the analysis mode the sample air flow is stopped. A carrier gas is introduced through line 5 into the collection and vaporization cell 3. The carrier gas passes through the cell and into the gas analyzer 7. The metal strip on which the particles have been deposited, located inside the cell 3, is rapidly heated by capacitor discharge. The heating process is less than a few seconds. The deposited particles are vaporized and the evolved species are carried to a gas-phase analyzer 7 for quantitation.

By selection of the carrier gas and the amount of heating, a selected constituent of the deposited particles $S_i$ is converted to a gas-phase species $C_i$ that may be quantitated by a standard commercial analyzer. The integral of the gas-phase concentration is proportional to the mass of the deposited species or element by the relation:

$$S_i \approx Q_c f_i MW_i\, v^- \int C_i dt$$

where:

$S_i$ is the mass of particle species i in ng;

$Q_c$ is the carrier gas flow rate into the gas phase analyzer in L/s;

$f_i$ is the empirical calibration factor;

$MW_i$ is the molecular weight of species i in g/mole;

$v$ is the molar volume of air in L;

$C_i$ is the gas phase concentration in ppb of the species into which the particle species Si is converted upon vaporization; and t is the integration time in s.

For analysis of sulfur-containing particlesr the species $C_i$ corresponds to gas-phase sulfur compounds that may be measured by flame photometric detection. Likewise particulate nitrate may be converted to nitrogen oxides, which may be analyzed by chemiluminescence using a molybdenum converter, Carbonaceous species may be converted to carbon dioxide which may be analyzed by commercial $CO_2$ detection methods. From the mass of the deposited species, the airborne concentration of the species (in $\mu g/m^3$) is obtained by dividing the mass Si (in ng) by the volume of sampled air (in L).

Flow switching between the sampling and analysis modes of operation is controlled by appropriate valves. For purposes of illustration one-way (on-off) valves are shown in FIG. 1, but other valve configurations are within the purview of this invention, such employment as of three-way valves may be used to accomplish the same purpose.

In FIG. 1 in sampling mode valve 8 to the pump is open and valves 9, 10 and 11 are closed. Additionally, valve 12 on the bypass line to the gas analyzer is open during the sampling mode. In analysis mode valve 8 to the pump is closed, and valves 9, 10 and 11 are open. Valve 12 is closed.

The system is controlled by computer or microprocessor 13, which controls the switching of the valves, the heating of the metal strip and the integration of the signal from the gas analyzer.

Except for the collection and vaporization cell 3, all of the components of the system use standard technology. The integrated collection and vaporization cell 3 is new technology unique to this invention.

Figure 2:
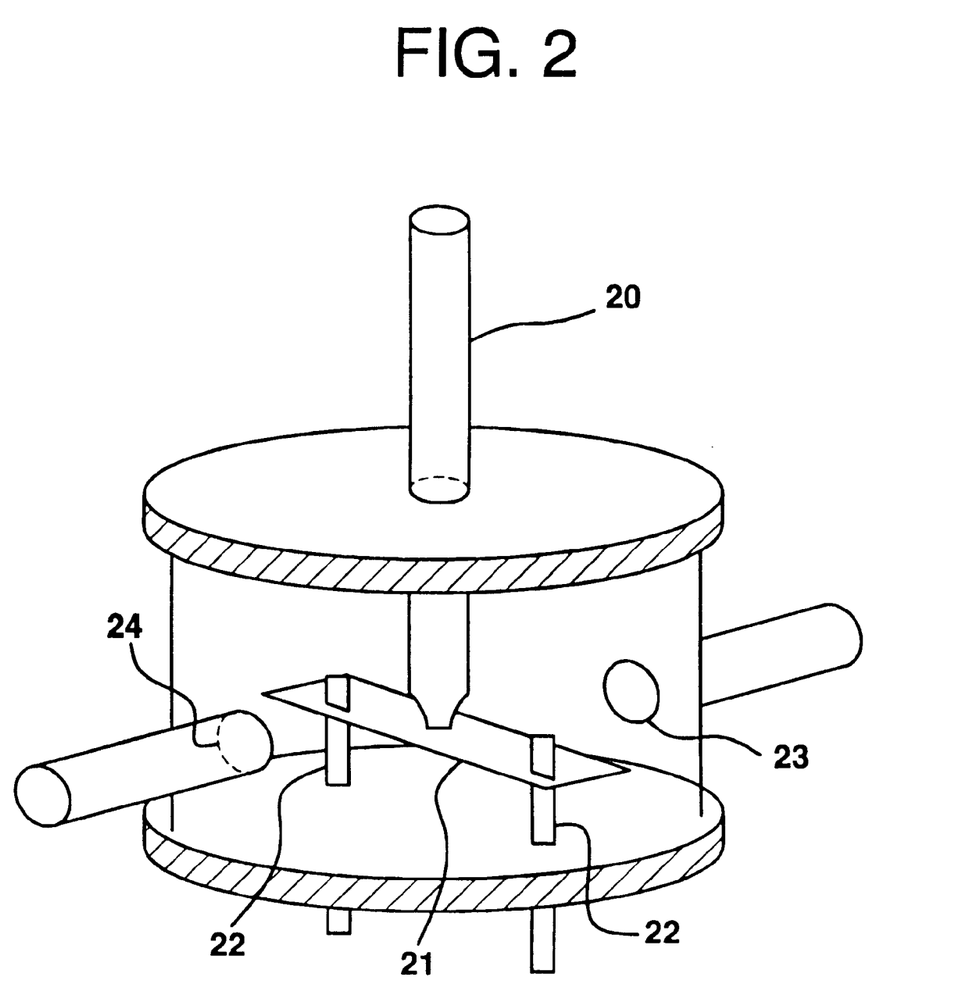
FIG. 2 is a perspective view of the integrated collection and vaporization cell.

A preferred cell is illustrated in FIG. 2. In sampling mode, humidified air enters the orifice tube 20, and is deposited by impaction on the metal strip 21. The strip is held in place by mounting posts 22 which provide electrical contact as well as mechanical stability. The pumping port 23, is at the side. In analysis mode the carrier gas is introduced into the cell through the orifice tube 20 and through the pumping port 23 and flows out through the analyzer port 24. The mounting posts 22 are electrically conducting, and provide the electrical path for the rapid heating of the strip.

Figure 3:
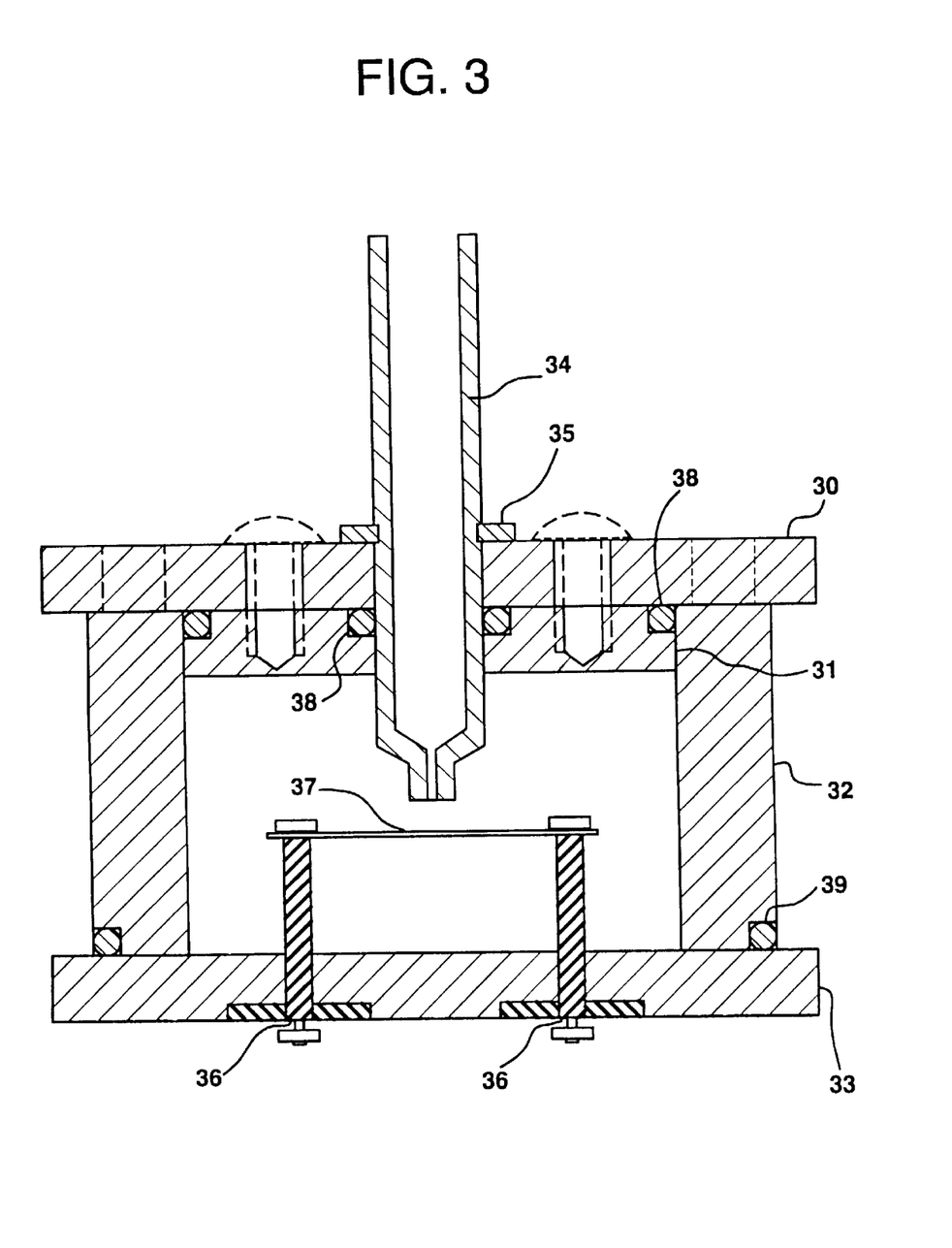
FIG. 3 is a cross section of the side view of an embodiment of the integrated collection and vaporization cell.
Figure 4:
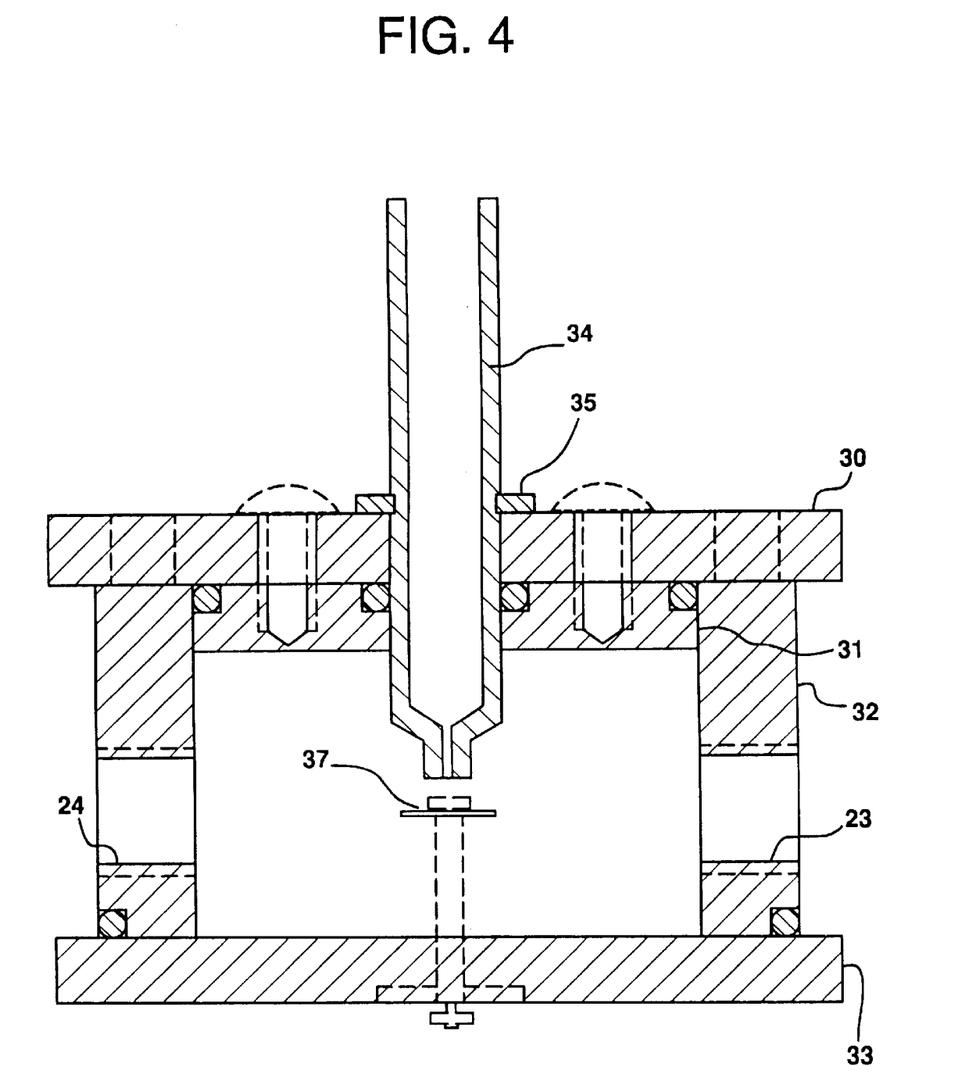
FIG. 4 is a cross section of the front view of an embodiment of the integrated collection and vaporization cell.

One preferred embodiment of the collection and vaporization cell is illustrated in side view in FIG. 3 and in front view in FIG. 4. The overall dimensions of a preferred cell are approximately 50 mm in diameter by 80 mm high. The cell top pieces 30 and 31, the cell body 32 and the cell bottom 33 are preferably made of clear polycarbonate and acrylic. The orifice tube 34 is made of stainless steel, with an orifice diameter of 0.368 mm (0.0145 in). O-rings 38 between the pieces 30 and 31 provide a vacuum seal against the orifice tube 34 and against the body pieces 32. Another O-ring 39 seals the body piece to the cell bottom 33. A retaining ring 35 holds the orifice tube in position. The mounting posts 36 are preferably metal with about 3–48 threads at each end. The preferred metal strip 37 is fabricated from type 302 stainless steel shim stock, and measures 5 mm×23 mm×0.0254 mm. The strip is mounted using 2 mm diameter holes located at either end of the strip (separated by 16 mm) and is secured using nuts and washers.

The particle collection efficiency of the cell has been measured in the laboratory using monodisperse ammonium sulfate particles. The particles were generated by nebulization, and monodisperse fraction was selected from the nebulized aerosol using a differential mobility analyzer. Particle concentration upstream of the collection cell was monitored with a condensation nucleus counter. Particle concentrations downstream of the collection cell were monitored with an optical particle counter operating at reduced pressure.

Figure 5:
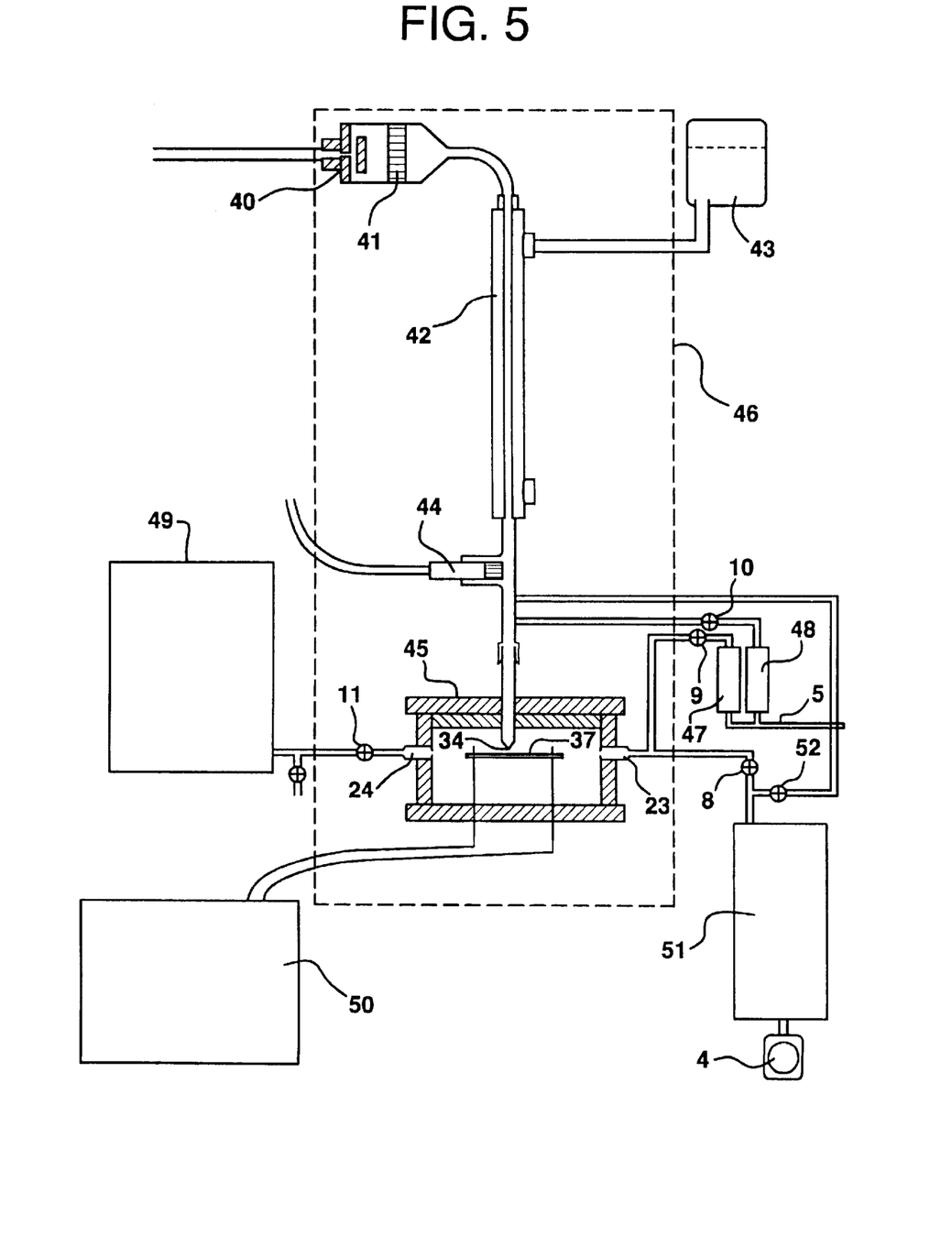
FIG. 5 is a schematic of the invention for the automated analysis of nitrate particles.

Particle penetration was determined from the ratio of the downstream particle counts with the orifice in place, to that with the orifice tube retracted to a jet-to-plate spacing of 11 mm. All counts were normalized to the upstream condensation nucleus counter concentrations. Collection efficiency was calculated as one minus the fraction of particles penetrating. Particle collection efficiency was found to be dependent, to some extent, on the jet-to-plate spacing. For example, for a jet-to-plate spacing of 1.9 mm particle collection efficiencies were above 95% for particle diameters ranging from 0.1 $\mu$m to 0.8 $\mu$m. All measurements were made with the orifice diameter of 0.368 mm and for a relative humidity of 88% immediately upstream of the The automated sampling and analysis of particles using the integrated collection and vaporization cell was first constructed as shown in FIG. 5. This system is used to measure the airborne concentration of nitrate in particles smaller than 3 $\mu$m in diameter. Ambient air is sampled at a flow rate of 1 L/min. The particle-laden air is pulled through a pre-impactor 40 to remove particles above 3 $\mu$m. Next the air passes through a multi-tube denuder 41 to remove nitric acid and peroxyi-acetalnitrate, as described in the literature. A multitube activated carbon denuder is preferred; a KOH coated multitube glass diffusion denuder has been used.

The air then passes through a commercially available humidifier 42, (Model MH110-12 Perma Pure Inc., Toms River, N.J.). The humidifier is operated with water in the annular space outside of the Nafion® transport membrane. The water jacket is kept full by means of the water reservoir 43. Temperature and relative humidity are measured by the probe 44. After passing through the humidifier, the airstream enters the integrated collection and vaporization cell 45. The orifice 34 is operated under sonic (choked) flow conditions, and the particles impact onto the stainless steel strip 37. The entire pre-impactor, denuder, humidifier and collection-analysis cell are housed in a box 46 which is ventilated with outside air so as to maintain sampling temperatures close to ambient temperature, After sample collection the system switches from the sampling mode to the analysis mode. The analysis mode takes just under 2 minutes. In analysis mode the pumping is switched to a bypass line and the cell is flushed with nitrogen gas. The carrier gas is introduced in slight excess of that required by the gas analyzer.

The nitrogen flow enters the cell through the orifice tube 34 and through the pumping port 23. Both nitrogen flows are metered by flow meters 47 and 48. For this embodiment, the gas analyzer sample rate is 0.6 L/min. To provide this flow to the gas analyzer approximately 0.45 L/min is introduced through the pumping port and approximately 0.2 L/min of nitrogen is directed to the orifice tube. The slight excess flow is vented upwards through the sampling line. That split gave the best system performance. With that flow configuration it is not necessary no close off the aerosol sampling line during the analysis.

In the preferred embodiment, in the analysis mode the nitrogen exiting the cell at 24 passes into a commercial chemiluminescence gas-phase nitrogen oxide analyzer 49 (Model 42C, Thermo Environmental Instruments, Franklin, Mass.). The analyzer is operated in manual $NO_x$ mode whereby the sampled stream passes through a molybdenum converter prior to detection. After the cell has been flushed with nitrogen, the strip is rapidly heated by capacitor discharge across the strip using conventional electronics 50. The strip was momentarily heated to a dull red color. The evolved nitrogen oxides are quantitated by the chemiluminescence analyzer.

For the above embodiment the system was controlled using a PC-XT clone computer equipped with an analog to digital and counter timer data acquisition card. The data acquisition program is written in Basic using standard technology. The program controls the switching of the solenoid valves, times the flushing of the cell, triggers the charging and discharging of the capacitors, captures and integrates the signal from the chemiluminescence analyzer, and records analog signals. User-selectable parameters include the sampling interval, the carrier gas flushing time and the integration interval.

During operation of this prototype system, particle collection efficiencies were checked by means of an optical particle counter 51 (particle Measuring Systems Model LPS-A-101, Boulder, Colo.) which operated at low pressure, between the collection cell. and pump 4. This is a diagnostic tool, and is not necessary to the system operation. An additional valve 52 was installed so that the optical counter could sample ambient particles during the analysis mode.

The response to nitrates is calibrated by application of liquid standards of sodium nitrate and ammonium nitrate to the stainless steel strip. To check the lack of response to ammonium ion, standards of ammonium sulfate were also applied. These standards were dried, and then analyzed in the cell using the automated system. Results show a nearly linear response to sodium nitrate, and a nearly equal response to ammonium nitrate.

While the invention has been described with reference to specific embodiments, modifications and variations of the invention may be constructed without departing from the scope of the invention, which is defined in the following claims.

We claim:

1. Automated particle chemistry monitor apparatus comprising:

a valveless sample gas inlet;

an integrated collection and vaporization cell for collecting and vaporizing particles from sample gas; an impaction collector in the cell; a sample gas director connected to the inlet and to the cell for directing sample gas and particles in the sample gas to the collector;

a port in the cell for withdrawing sample gas from the cell;

a pump connected to a port in the cell for drawing sample gas through the cell;

a carrier gas source connected to the cell for flowing carrier gas into the cell;

a power source connected to the collector for rapidly heating the collector and converting the collected particles to vapors;

a port in the cell for withdrawing carrier gas and vapors from the cell; and an analyzer connected to the port for analyzing concentration of chemical or elemental constituent obtained from vaporization of the particles, wherein no valves exist between the inlet and the cell.

2. The apparatus of claim 1, further comprising a cell bypass connected between the inlet and the pump for bypassing the sample gas around the cell during flowing of the carrier gas.

3. The apparatus of claim 1, further comprising a humidifier connected between the inlet and the cell for humidifying the sample gas.

4. The apparatus of claim 1, further comprising a preimpactor connected between the inlet and the cell for removing large particles from the sample gas.

5. The apparatus of claim 1, further comprising a denuder connected between the inlet and the cell for removing compounds from the sample gas.

6. The apparatus of claim 1, further comprising a ventilated housing surrounding the cell and upstream components for maintaining sample gas temperature near ambient temperature.

7. The apparatus of claim 1, further comprising a temperature and humidity probe connected to the sample gas director for measuring temperature and humidity of the sample gas.

8. The apparatus of claim 1, wherein carrier gas source is a carrier gas source mostly devoid of oxygen for vaporizing the sample gas in the cell without oxidation.

9. The apparatus of claim 1, further comprising a preconditioner connected between the inlet and the cell for preconditioning the sample gas by adding condensible vapor to the sample gas.

10. The apparatus of claim 1, wherein no valves exist between the inlet and the cell.

11. A Method for integrated collection and vaporization for particle collection and measurement comprising:

providing a sample gas inlet providing a collector and vaporizer cell with an impaction collector in the cell;

directing sample gas and particles from the inlet to the impaction collector;

adding condensable vapor to the sample gas for preconditioning the sample gas before directing the sample gas and particles to the impaction collector;

collecting airborne particles from sample gas on the impaction collector;

withdrawing sample gas from the cell; flowing carrier gas into the cell; heating rapidly the impaction collector and converting the particles to vapors;

withdrawing carrier gas and vapors from the cell; and measuring the amount of vapors or elemental constituents obtained from vaporization of the particles.

12. The method of claim 11, further comprising bypassing the sample gas around the cell during the heating, flowing and measuring.

13. The method of claim 11, further comprising humidifying the sample gas.

14. The method of claim 11, further comprising removing large particles from the sample gas by preimpaction.

15. The method of claim 11, further comprising denuding the sample gas and removing compounds from the sample gas.

16. The method of claim 11, further comprising maintaining sample gas temperature near ambient temperature by surrounding the cell and upstream components with a ventilated housing.

17. The method of claim 11, wherein the flowing of carrier gas comprises flowing the carrier gas into the cell through the director as well as through a separate port in the cell.

18. The method of claim 11, further comprising measuring temperature and humidity of the sample gas.

19. The method of claim 11, wherein the flowing of carrier gas comprising flowing the carrier gas into the cell mostly devoid of oxygen.

20. The method of claim 11, further comprising adding condensible vapor to the sample gas for preconditioning the sample gas before directing the sample gas and particles to an impaction collector.

21. The method of claim 11, wherein the steps of directing of sample gas and particles to an impaction collection and withdrawing sample gas from the cell involve no valves between the inlet and the cell.

22. The apparatus of claim 1, the integrated collection and vaporization cell further comprising a collection and vaporization cell body with a top, a bottom, and a body side wall connecting to the top and the bottom, wherein the director further comprises at least one sample gas directing orifice tube connected to the cell, wherein the ports are connected to the side wall of the cell, and wherein the impaction collector further comprises a metallic sampling strip mounted in the cell.

23. The apparatus of claim 22, wherein the strip is stainless steel, and further comprising metal mounting posts extending upward from the cell bottom for mounting the strip, wherein the mounting posts are electrically conductive for providing an electrical path to the strip for heating the strip.

24. The apparatus of claim 22, wherein one port is a pumping port and another port is an analyzer port.

25. A method of particle sampling comprising providing a collector having a collection and vaporization cell, mounting a strip in the cell, supplying sampling substance to the cell by a tube, depositing the particles in the sampling substance on the strip by impaction, directing the sampling substance through a pumping port in the cell, bypassing the sampling substance around the cell, flowing a carrier gas into the cell, heating the strip and vaporizing substance collected on the strip, conducting the carrier gas and vapors produced by the vaporizing from the cell to an analyzer and analyzing concentration of chemical or elemental constituents in the vapors.

26. The method of claim 25, wherein the mounting comprises mounting the strip on conductive posts, connecting the posts to a power source, and heating the strip.

27. The method of claim 25, further comprising connecting the cell to a controller for automatically switching the collector from a sampling mode to an analysis mode.

28. The method of claim 25, further comprising switching the collector to the analysis mode, supplying carrier gas to the cell, analyzing and determining a concentration of particles in a sampled gas by means of an analyzer connected to the collector.

29. The method of claim 25, wherein the analyzing comprises analyzing for nitrate.

30. The method of claim 25, wherein the analyzing comprises analyzing for sulfur.

31. The method of claim 25, wherein the carrier gas is mostly devoid of oxygen.

32. The method of claim 25, wherein the flowing comprises flowing of carrier gas directly into the cell and indirectly into the cell via a sampling substance supplying route.

33. The method of claim 25, further comprising preconditioning the sampling substance by adding condensible vapor to the sampling substance.

34. The method of claim 25 wherein the supplying comprises supplying a sample with airborne nitrate or sulfate containing particles to the cell.

35. The method of claim 34, further comprising humidifying the sample before the cell, and wherein the depositing comprises impacting the nitrate or sulfate containing particles on the strip.

36. The method of claim 34, wherein the vaporizing and analyzing comprises vaporizing the nitrate or sulfate in the particles to NO, $NO_2$ or $SO_2$ for analyzing.

37. An integrated collection and vaporization particle chemistry monitoring apparatus comprising:
  a sample inlet;
  a sample conduit connected to the inlet;
  a cell connected to the sample conduit;
  a nitrate or sulfate particle impaction collector in the cell;
  a pump connected to the cell for withdrawing sample fluid from the cell;
  a source of carrier gas connected to the cell for flowing the vapors from the cell;
  a power source connected to the cell for rapidly heating and vaporizing the nitrate and sulfate in the collected particles into vapors of nitrogen or sulfur compounds; and
  an analyzer connected to the cell for receiving the vapors and carrier gas and for analyzing the vapors for nitrate or sulfur compounds.

38. The apparatus of claim 37, wherein the sample conduit is devoid of valves.

39. The apparatus of claim 37, wherein the carrier gas source is connected separately to the sample conduit and to the cell.

40. The apparatus of claim 37, further comprising a sample humidifier connected to the sample conduit.

41. The apparatus of claim 37, wherein carrier gas source is a carrier gas source mostly devoid of oxygen for vaporizing the particles in the cell without oxidation.

42. The apparatus of claim 37, further comprising a cell bypass connected between the inlet and the pump for bypassing the sample around the cell during flowing of the carrier gas.

43. The apparatus of claim 37, further comprising a preconditioner connected to the sample conduit between the sample inlet and the cell for preconditioning the sample by adding condensible vapor to the sample.

44. An integrated collection and vaporization particle chemistry monitoring method comprising:
  providing a sample inlet;
  conducting the sample through a sample conduit to a cell;
    impacting and collecting nitrate or sulfate particles in the cell;

withdrawing sample fluid from the cell;

flowing a carrier gas into the cell;

vaporizing the collected nitrate or sulfate particles into vapors of nitrogen or sulfur compounds;

flowing the vapors and the carrier gas from the cell;

receiving the vapors and carrier gas in a an analyzer; and analyzing the vapors for nitrate or sulfur compounds.

45. The method of claim 44, wherein the conducting of the sample conduit is in the absence of valves.

46. The method of claim 44, wherein the flowing of the carrier gas is directly to the cell and indirectly through the sample conduit to the cell.

47. The method of claim 44, further comprising humidifying the sample in the conduit.

48. The method of claim 44, wherein the flowing of the carrier gas is flowing of the carrier gas mostly devoid of oxygen and wherein the vaporizing of the particles in the cell is without oxidation.

49. The method of claim 44, further comprising bypassing the sample around the cell during the flowing of the carrier gas.

50. The method of claim 44, further comprising preconditioning the sample by adding condensible vapor to the staple in the conduit.

* * * * *